United States Patent
Yoshioka

(10) Patent No.: US 9,351,885 B2
(45) Date of Patent: May 31, 2016

(54) DISPOSABLE WEARING ARTICLE

(71) Applicant: Unicharm Corporation, Ehime (JP)

(72) Inventor: Toshiyasu Yoshioka, Kagawa (JP)

(73) Assignee: Unicharm Corporation, Ehime (JP)

( * ) Notice: Subject to any disclaimer, the term of this patent is extended or adjusted under 35 U.S.C. 154(b) by 124 days.

(21) Appl. No.: 14/344,547

(22) PCT Filed: Sep. 27, 2012

(86) PCT No.: PCT/JP2012/006204
§ 371 (c)(1),
(2) Date: Mar. 12, 2014

(87) PCT Pub. No.: WO2013/046701
PCT Pub. Date: Apr. 4, 2013

(65) Prior Publication Data
US 2015/0011958 A1    Jan. 8, 2015

(30) Foreign Application Priority Data
Sep. 30, 2011    (JP) ................. 2011-218056

(51) Int. Cl.
*A61F 13/15*    (2006.01)
*A61F 13/20*    (2006.01)
(Continued)

(52) U.S. Cl.
CPC ..... *A61F 13/49012* (2013.01); *A61F 13/15203* (2013.01); *A61F 13/496* (2013.01);
(Continued)

(58) Field of Classification Search
CPC .............. A61F 13/49007; A61F 13/49009; A61F 13/49011; A61F 2013/49007; A61F 2013/49009; A61F 2013/49036; A61F 13/49012
USPC ........................ 604/385.24, 385.27
See application file for complete search history.

(56) References Cited

U.S. PATENT DOCUMENTS 7,347,847 B2    3/2008    Toyoshima et al.
2004/0030317 A1*    2/2004    Torigoshi .......... A61F 13/49014
604/385.27

(Continued)

FOREIGN PATENT DOCUMENTS

EP    1 184 012 A1    3/2002
JP    2001-061890    3/2001

(Continued)

OTHER PUBLICATIONS

European supplementary Search Report from corresponding European application No. 12836440.3 dated Jul. 3, 2015 (7 pgs).

(Continued)

*Primary Examiner* — Michele M Kidwell
(74) *Attorney, Agent, or Firm* — Brinks Gilson & Lione

(57) ABSTRACT

A disposable wearing article in which waist elastics are attached at least in a rear waist region of front and rear waist regions so that a space between a core and the wearer's skin is formed which functions as a pocket for retaining excretions such as feces or the like. A diaper includes front and rear waist panels in which front and rear waist elastics are attached and a crotch panel extending therebetween. With regard to the crotch panel, front and rear end edges are joined to the skin facing sides of the front and rear waist panels respectively such that the front and rear end edges of the core are overlapped with the front and rear waist panels. In the front and rear waist panels, inelastic regions, first elastic regions, and second elastic regions are formed respectively. In the crotch panel, a pair of first cuffs in which the gasket elastics is attached are formed, and the front and rear end portions are intersected with the front and rear waist elastics in the gasket elastics.

20 Claims, 7 Drawing Sheets

(51) Int. Cl.
*A61F 13/49* (2006.01)
*A61F 13/496* (2006.01)
*A61F 13/494* (2006.01)

(52) U.S. Cl.
CPC ..... *A61F13/49017* (2013.01); *A61F 13/49413* (2013.01); *A61F 2013/15357* (2013.01); *A61F 2013/4948* (2013.01)

(56) References Cited

U.S. PATENT DOCUMENTS

| | | | |
|---|---|---|---|
| 2004/0133181 A1* | 7/2004 | Ishiguro | A61F 13/49001 604/385.28 |
| 2004/0243089 A1 | 12/2004 | Veith et al. | |
| 2005/0126689 A1 | 6/2005 | Thorson et al. | |
| 2005/0203479 A1 | 9/2005 | Sakaguchi et al. | |
| 2009/0088718 A1* | 4/2009 | Toyoshima | A61F 13/49011 604/385.23 |
| 2010/0076394 A1* | 3/2010 | Hayase | A61F 13/15593 604/385.29 |
| 2011/0071488 A1* | 3/2011 | Kuwano | A61F 13/49001 604/385.3 |
| 2012/0289921 A1 | 11/2012 | Hashino et al. | |

FOREIGN PATENT DOCUMENTS

| | | |
|---|---|---|
| JP | 2004-290646 | 10/2004 |
| JP | 2006-167351 | 6/2006 |
| JP | 2010-075463 | 4/2010 |
| JP | 2011-136082 | 7/2011 |
| JP | 2012-061186 | 3/2012 |
| WO | WO 2006/001737 A1 | 1/2006 |

OTHER PUBLICATIONS

International Search Report from corresponding PCT application No. PCT/JP2012/006204 dated Dec. 18, 2012 (2 pgs).

* cited by examiner

DISPOSABLE WEARING ARTICLE

RELATED APPLICATION

This application is a 35 U.S.C. §371 national phase filing of International Patent Application No. PCT/JP2012/006204, filed Sep. 27, 2012, through which and to which priority is claimed under 35 U.S.C. §119 to Japanese Patent Application No. 2011-218056, filed Sep. 30, 2011.

TECHNICAL FIELD

The present disclosure relates to disposable wearing articles, more specifically, relates to disposable wearing articles such as disposable diapers, disposable toilet training pants, disposable incontinent pants, disposable sanitary pants, or the like.

BACKGROUND

Disposable diapers which include an absorbent structure extending from a crotch region into front and rear waist regions and elastics attached in the front and rear waist regions are known. For example, JP 2001-61890 A (PTL 1) discloses a disposable diaper in which waist elastic members are attached to the waist opening, and the waist elastic members exert elasticity in regions in which the absorbent structure is not positioned, while in a region in which the absorbent structure is positioned, the elasticity is substantially not exerted.

CITATION LIST

Patent Literature

{PTL 1}
JP 2001-61890 A

SUMMARY

Technical Problem

The PTL 1 does not teach what shape the absorbent structure may assume by the contraction of elastic members attached in the waist regions.

Solution to Problem

Some embodiments of the present invention provide a disposable wearing article having a longitudinal direction and lateral direction, including: a skin facing side and a non-skin facing side opposite thereto; front and rear waist regions; a crotch region located between the front and rear waist regions; a first waist panel which defines one of the front and rear waist regions and is elastically contractible in the lateral direction; a second waist panel which defines the other of the front and rear waist regions and is elastically contractible in the lateral direction; a crotch panel extending between the first and second waist panels in the longitudinal direction to define a crotch region; and a body fluid absorbent structure located in the crotch panel.

The body fluid absorbent structure includes a liquid-absorbent core and liquid-permeable covering sheet covering the core. The crotch panel is provided with first and second panel-end edges extending in the lateral direction and joined to the skin facing side of the first and second waist panels respectively. The core is provided with first and second core-end edges each extending in the lateral direction and at least the second core-end edge thereof overlaps with the second waist panel. The second waist panel is provided with an inelastic region defined in a region overlapping with the core. A first elastic region is formed outboard of the inelastic region in the lateral direction. A second elastic region is formed outboard of the inelastic region in the longitudinal direction. A distance between the second elastic region and the second core-end edge is 5 to 20 mm.

DESCRIPTION OF EMBODIMENTS

Figure 1:
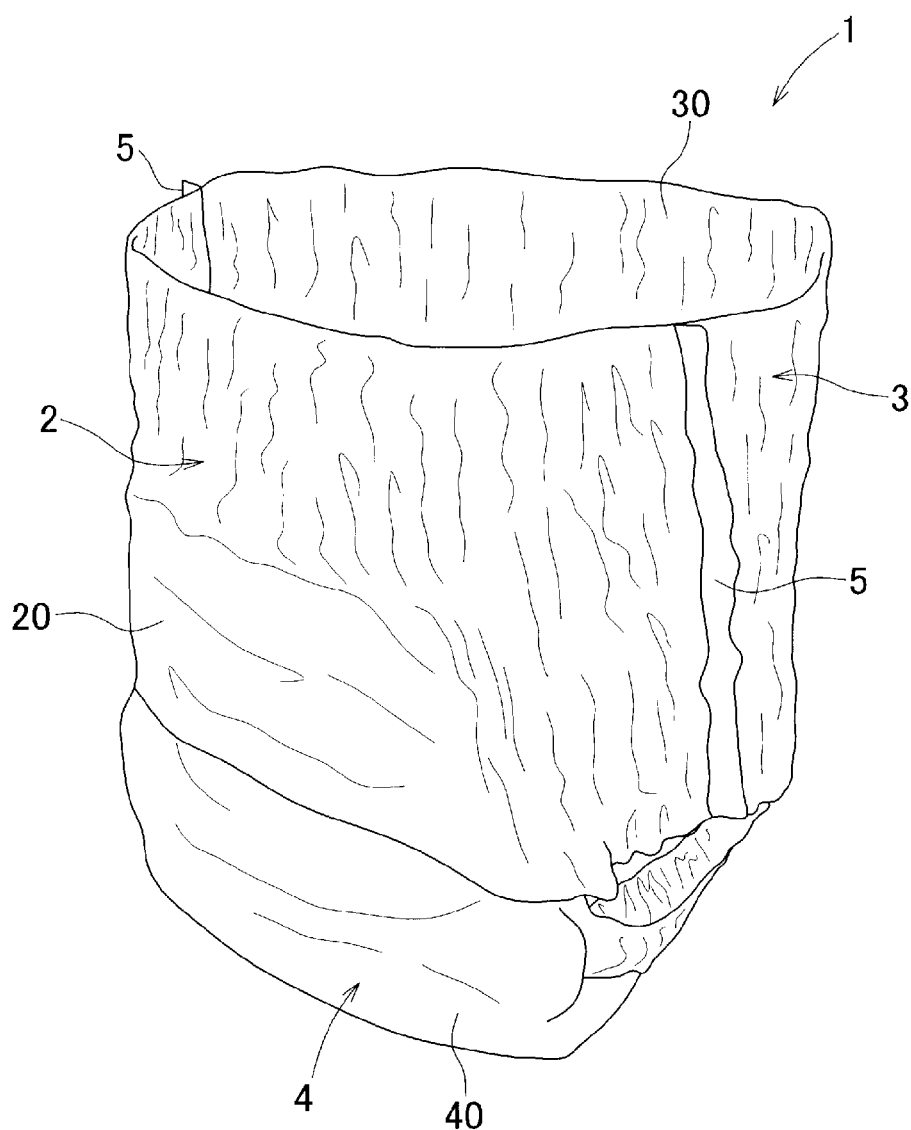
FIG. 1 is a perspective view of a diaper as one example of disposable wearing articles seen from a front waist region side.
Figure 2:
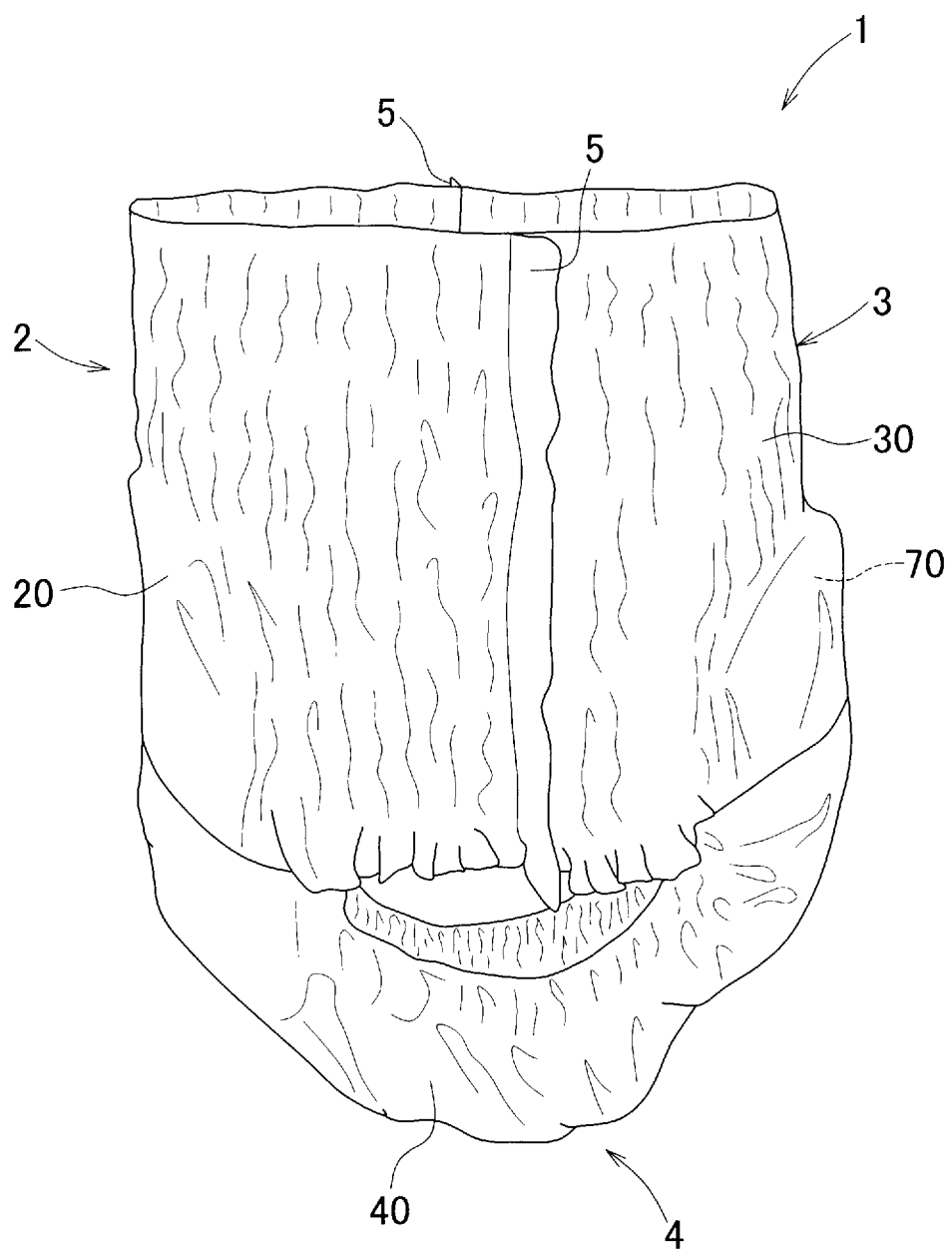
FIG. 2 is a perspective view seen from a side of the diaper.
Figure 3:
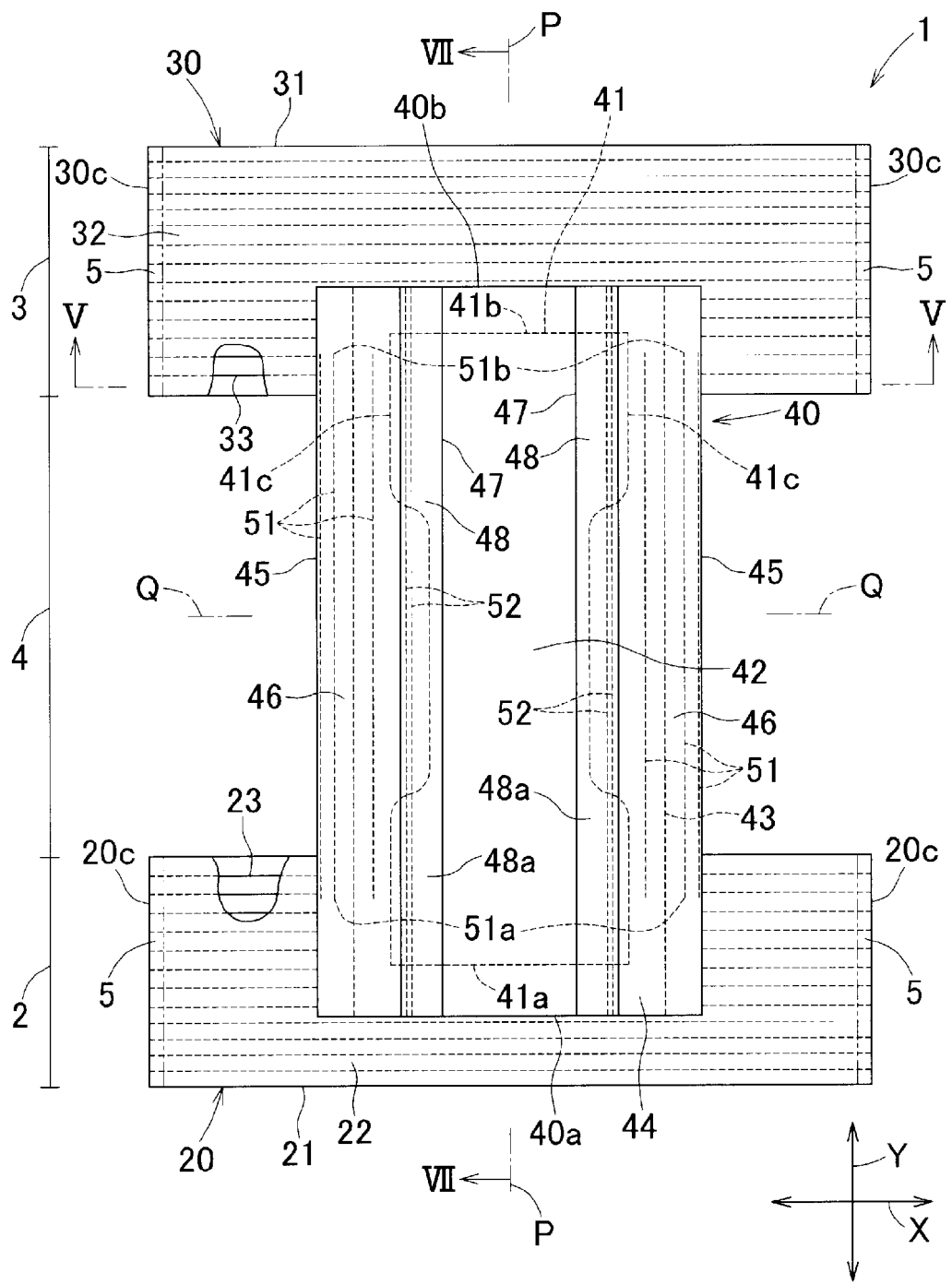
FIG. 3 is a developed plan view seen from a skin facing side of the diaper.
Figure 4:
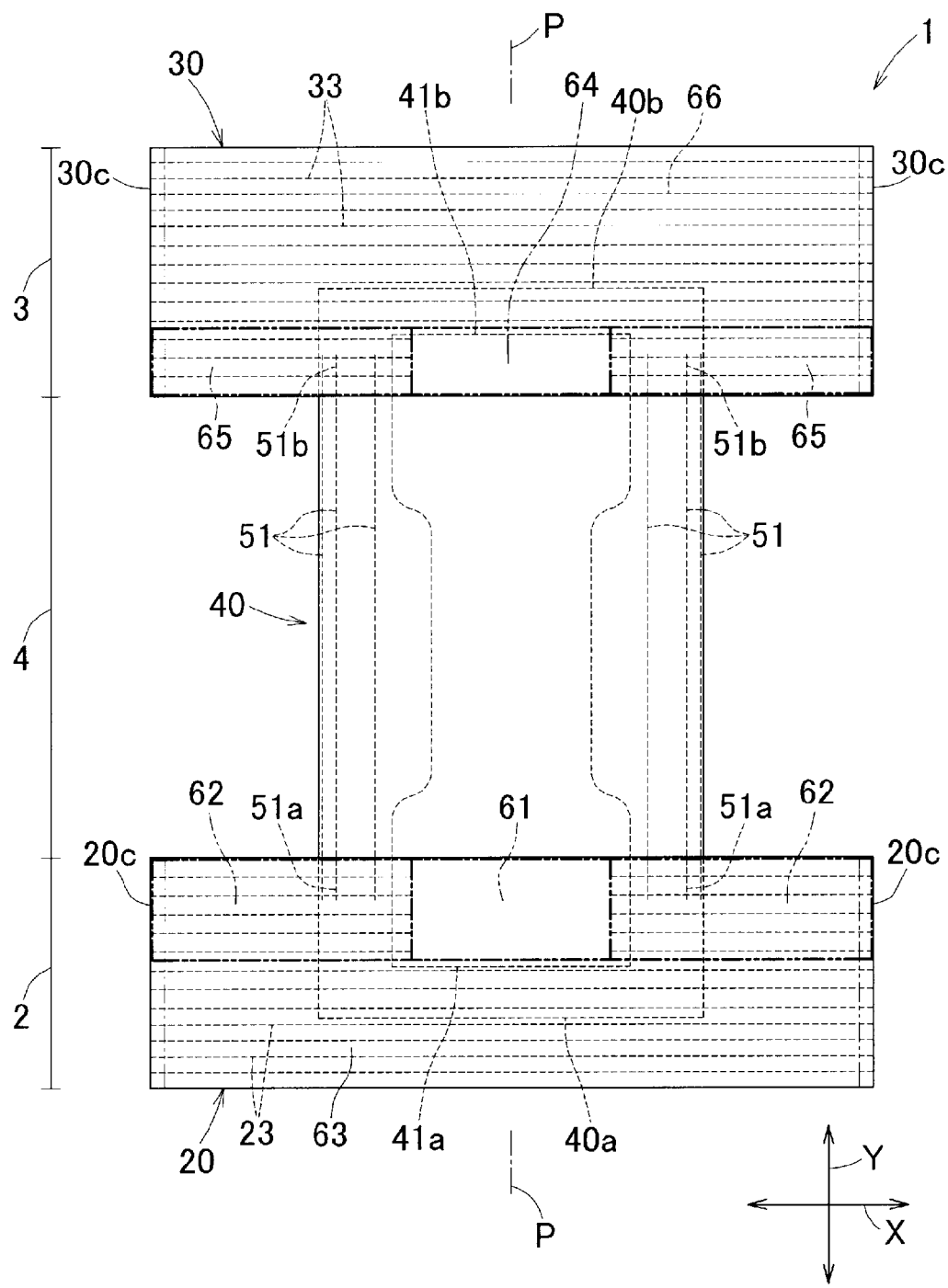
FIG. 4 is a developed plan view seen from a non-skin facing side of the diaper.
Figure 5:
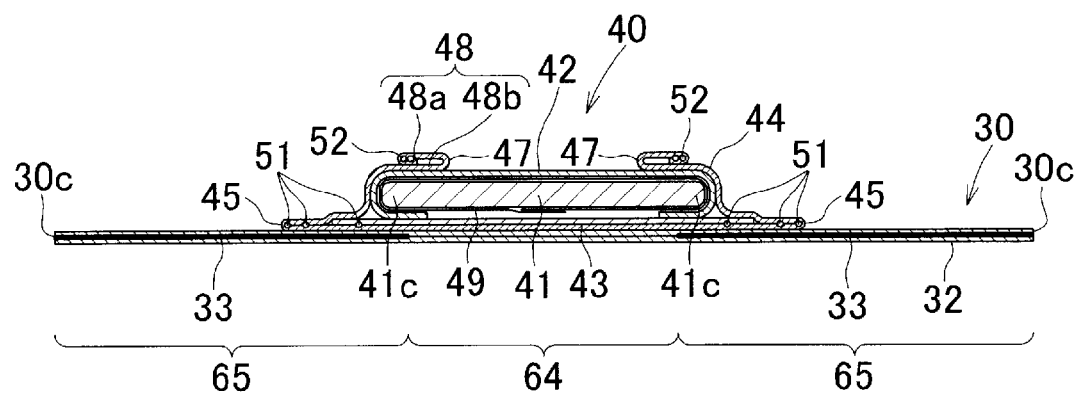
FIG. 5 is a cross section view along V-V line of FIG. 3.

Referring to FIG. 1 to FIG. 5 and FIG. 7, the diaper 1 includes a skin facing side and a non-skin facing side opposite thereto, a front waist region 2, a rear waist region 3, and a crotch region 4 extending between the front and rear waist regions 2, 3. The diaper 1 includes in a developed plan view an imaginary longitudinal center line P-P bisecting a dimension in a lateral direction X and an imaginary lateral center line Q-Q bisecting a dimension in a longitudinal direction Y, and is symmetrical about the imaginary longitudinal center line P-P. In FIGS. 3, 4, respective elastics are illustrated in a stretched state against the contractile force thereof.

The diaper 1 further includes a front waist panel 20 defining the front waist region 2, a rear waist panel 30 defining the rear waist region 3, and a crotch panel 40 defining the crotch region 4 and extending to the front and rear waist regions 2, 3. The front waist panel 20 includes a front waist sheet 22 folded along a folding line 21 extending in the lateral direction X and front waist elastics 23 attached between the folded front waist sheets 22. The front waist elastics 23 extend in the lateral direction X and are contractibly attached in a stretched state so as to elasticize the front waist panel 20 in the lateral direction X. The folded front waist sheets 22 are attached to each other by known bonding means such as a hot melt adhesive via the front waist elastics 23.

The rear waist panel 30 includes a rear waist sheet 32 folded along a folding line 31 extending in the lateral direction X and rear waist elastics 33 attached between the folded rear waist sheets 32. The rear waist elastics 33 extend in the lateral direction X and are contractibly attached in a stretched state so as to elasticize the rear waist panel 30 in the lateral direction X. The folded rear waist sheets 32 are attached to each other by known bonding means such as a hot melt adhesive via the rear waist elastics 33.

These front and rear waist panels 20, 30 are annularly joined by a series of seams 5 formed along the lateral edges 20c, 30c, thereby forming a waist opening.

As the front and rear waist sheets 22, 32, for example, a spunbonded nonwoven fabric or a spunbonded-meltblown-spunbonded (SMS) nonwoven fabric having a mass per unit area of about 10 to about 40 g/m², preferably about 11 to about 20 g/m² may be used. As the front and rear waist elastics, a plurality of thread, string or strand elastics may be used. For example, elastics of about 400 to about 1200 dtex are disposed at a pitch of about 4 to about 12 mm in the longitudinal direction Y so as to be attached at a stretch ratio of about 1.7 to about 3.5.

The crotch panel 40 includes a body side liner 42 attached on an absorbing side of the core 41; a leakage-barrier sheet 43 attached on a bottom side of the core 41; an absorbent structure including the core 41 and a covering sheet 49 to cover the core 41; and a back sheet 44 to cover the body side liner 42 and the leakage-barrier sheet 43 and to define the outer shape of a crotch panel 40. The body side liner 42, the leakage-barrier sheet 43 and the back sheet 44 have substantially equal dimensions in the longitudinal direction Y, defining the front and rear end edges 40a, 40b of the crotch panel 40 extending in the lateral direction X. The core 41 and covering sheet 49 have smaller dimensions in the longitudinal direction Y than those of the leakage-barrier sheet 43, the body side liner 42, the leakage-barrier sheet 43 and the back sheet 44. The front and rear end edges 41a, 41b of the core 41 extending in the lateral direction X and the front and rear end edges 49a, 49b of the covering sheet 49 extending in the lateral direction X are located inner than the front and rear end edges 40a, 40b of the crotch panel 40 in the longitudinal direction Y.

The back sheet 44 is attached to the leakage-barrier sheet 43 on the bottom side of the core 41, extends outboard of the lateral edges 41c of the core 41, and is folded toward the imaginary longitudinal center line P-P along the first folding line 45 extending in the longitudinal direction Y so as to form a pair of first cuffs (gasket cuff) 46 spaced apart from each other in the lateral direction X. Furthermore, the back sheet 44 is folded outwardly in the lateral direction X along a second folding line 47 extending in the longitudinal direction Y at a point to overlap with the core 41, thereby forming a pair of second cuffs 48 spaced apart from each other in the lateral direction X. In the first cuff 46, gasket elastics 51 extending in the longitudinal direction are contractibly attached in a stretched state. The back sheets 44 are attached to each other by known joining means such as a hot melt adhesive (not illustrated) in the first cuff 46. The first cuff 46 is primarily capable of staying in close contact with the wearer's thighs, while the second cuff 48 is, inside the first cuff 46, primarily capable of staying in close contact with the wearer's inguinal region or vicinities thereof, thereby preventing excretions from leaking sideways respectively.

The gasket elastics 51 is attached in such a manner that the front end portions 51a overlap with the front waist region 2 and intersect with the front waist elastics 23, while the rear end portion 51b overlap with the rear waist region 3 and intersect with the rear waist elastics 33. The fact that the front and rear end portions 51a, 51b intersect with the front and rear waist elastics 23, 33 means that they are indirectly overlapped via the front and rear waist sheets 22, 32 and the back sheet 44 to be intersected. With regard to the gasket elastics 51, the front and rear end portions 51a, 51b are located inner than the front and rear end edges 41a, 41b of the core 41 in the longitudinal direction Y, that is, they are located on the imaginary lateral center line Q-Q side. At least at the rear end portion 51b of the gasket elastics 51, a dimension to the rear end edge 41b of the core 41 in the longitudinal direction Y is about 5 to about 20 mm, preferably about 7 to about 15 mm.

The second cuff 48 has a proximal edge portion 48b joined to the body side liner 42 at the front and rear end portions thereof and a distal edge portion 48a not joined to the body side liner 42 so as to space away therefrom. In the distal edge portion 48a, a distal elastics 52 extending in the longitudinal direction Y is contractibly attached in a stretched state.

As the core 41, wood fluff pulp, superabsorbent polymer particles, or a mixture thereof may be used. As the covering sheet 49, a liquid-permeable and liquid dispersing sheet such as tissue paper or the like may be used. For example, a spun lace nonwoven fabric having a mass per unit area of about 10 to about 30 g/m² may be used. The core 41 and the covering sheet 49 may be joined to each other by using known joining means such as hot melt adhesives (not illustrated).

As a material of the body side liner 42, for example, a spunbond nonwoven fabric or a point bonded nonwoven fabric having a mass per unit area of about 15 to about 35 g/m², preferably about 18 to about 23 g/m² may be used. As the leakage-barrier sheet 43, a breathable and liquid-impermeable plastic film or laminate of the film and a nonwoven fabric may be used.

As the back sheet 44, for example, an SMS nonwoven or spunbond nonwoven fabric having a mass per unit area of about 10 to about 30 g/m² may be used. As the gasket elastics 51, a thread, strand or string elastics having about 400 to about 1200 dtex may be attached at a stretch ratio of about 2.0 to about 3.0. As the distal elastics 52, a thread, strand or string elastics having about 400 to about 1200 dtex may be attached at a stretch ratio of about 2.0 to about 3.0.

With regard to the above crotch panel 40, the front end edge 40a is located on the skin facing side of the front waist panel 20 and the back sheet 44 is joined to the front waist sheet 22 by known joining means such as a hot melt adhesive (not illustrated). At this time, the front end edge 41a of the core 41 is also located in the front waist region 2 such that part of the core 41 is overlapped with the front waist panel 20. A dimension in the longitudinal direction Y of the core 41 overlapping with the front waist panel 20 is about 50 to about 90 mm. In the region in which the core 41 is overlapped as described above, an inelastic region 61 in which the front waist elastics 23 are not positioned is formed. Also the inelastic region 61 may be formed by disposing no front waist elastics 23. Also it may be formed, after the continuous front waist elastics 23 are attached between the lateral edges 20c of the front waist panel 20, the elastics are cut off in the region overlapping with the core 41 so that the elastics are cut back and exert no elasticity.

Outboard of the inelastic region 61 in the lateral direction X, a first elastic region 62 is formed in such a manner that the elasticity of the front waist elastics 23 is exerted thereon. The first elastic region 62 is to partially overlap with the core 41. That is, part of the front waist elastics 23 is attached so as to overlap with the lateral edges 41c of the core 41, in which a dimension of the overlapping region in the lateral direction X is about 15 to about 35 mm. Accordingly, the contractile force of the front waist elastics 23 is exerted at the lateral edges 41c of the core 41.

Outboard of the inelastic region 61 in the longitudinal direction Y, a second elastic region 63 is formed in such a manner that the elasticity of the front waist elastics 23 is exerted thereon. The second elastic region 63 is formed by the front waist elastics 23 being continuous between the lateral edges 20c of the front waist panel 20.

Substantially in the entire region excluding the lateral edges 41c of the above core 41, the contractile force of the front waist elastics 23 is not exerted on the core 41, hence the core 41 does not shrink in the lateral direction X. Since no gathers are formed on the core 41, the area to contact with the wearer's skin is not decreased.

The rear end edge 40b of the crotch panel 40 is located on the skin facing side of the rear waist panel 30 and the back sheet 44 is joined to the rear waist sheet 32 by known joining means such as a hot melt adhesive (not illustrated). At this time, the rear end edge 41b of the core 41 is located the rear waist region 3 such that part of the core 41 is overlapped with the rear waist panel 30. A dimension of the core 41 in the longitudinal direction Y overlapping with the rear waist panel 30 is about 20 to about 50 mm, which is smaller than that of the front waist panel 20. In the region in which the core 41 is overlapped as described above, an inelastic region 64 in which the rear waist elastics 33 are not positioned is formed.

Outboard of the inelastic region 64 in the lateral direction X, a first elastic region 65 is formed in such a manner that the elasticity of the rear waist elastics 33 is exerted thereon. The first elastic region 65 is configured to partially overlap with the core 41. That is, part of the rear waist elastics 33 is attached so as to overlap with the lateral edges 41c of the core 41. More specifically, a dimension of the region in which they are overlapped in the lateral direction X is about 5 to about 20 mm. Accordingly, the contractile force of the rear waist elastics 33 is exerted at the lateral edges 41c of the core 41. However, the region in which the rear waist elastics 33 are overlapped with the lateral edges 41c of the core 41 in the rear waist region 3 is to be smaller than that of the front waist region 2.

Figure 6:
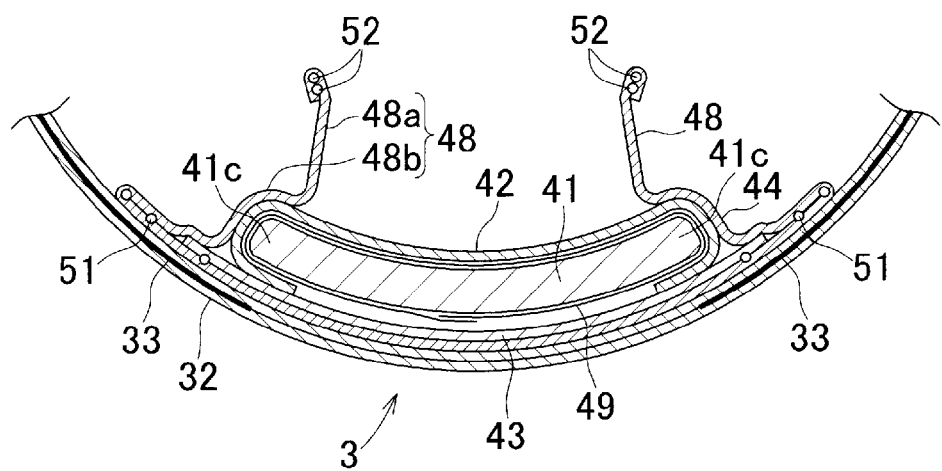
FIG. 6 is a diagram corresponding to FIG. 5 in a worn state.

As illustrated in FIG. 6, substantially in the entire region of the core 41 located in the rear waist region 3 excluding the lateral edges 41c, since the contractile force of the rear waist elastics 33 does not work on the core 41, the core 41 does not shrink in the lateral direction X, thereby the area capable of facing the skin is never decreased. Accordingly, it is possible to prevent the absorbing capacity from decreasing caused by a decrease in the area facing the skin. While the first elastic region 65 is in close contact with the wearer's skin by the contractile force, the inelastic region 64 is not in close contact with the skin, in which it bends with the lateral edges 41c as a base point so as to be spaced away from the wearer's skin. In particular, since at the lateral edges 41c of the core 41, the rear waist elastics 33 are overlapped and joined, the stiffness thereof becomes larger in the vicinity of the lateral edges 41c than in other regions such that it more easily bends in the center of the core 41 having low stiffness in a direction spaced away from the skin. In the front waist region 2, since the region in which the front waist elastics 23 overlap with the lateral edges 41c is relatively large, the core 41 is pushed toward the wearer's skin by the contractile force of the elastics, hence it is not spaced away from the wearer's skin.

Figure 7:
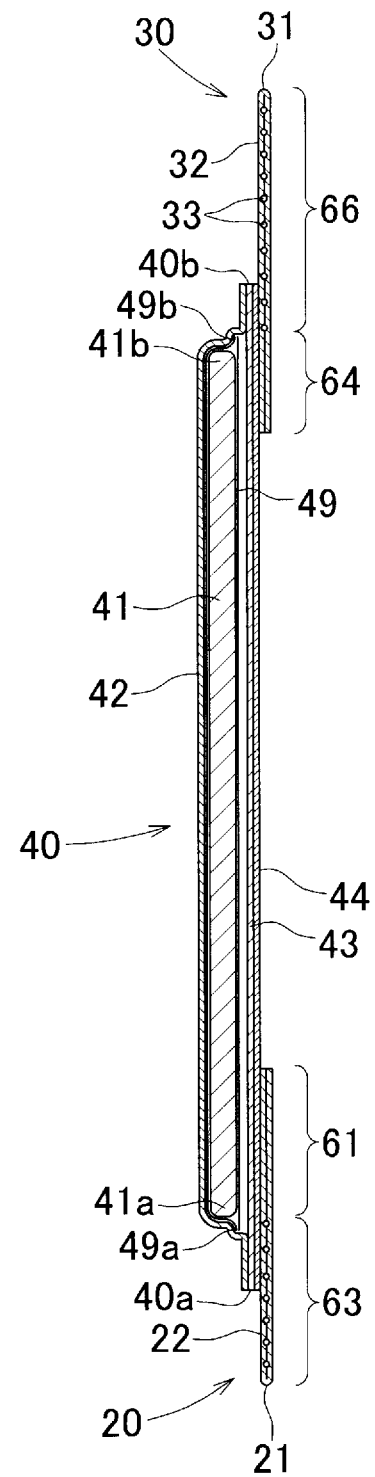
FIG. 7 is a cross section view along VII-VII line of FIG. 3
Figure 8:
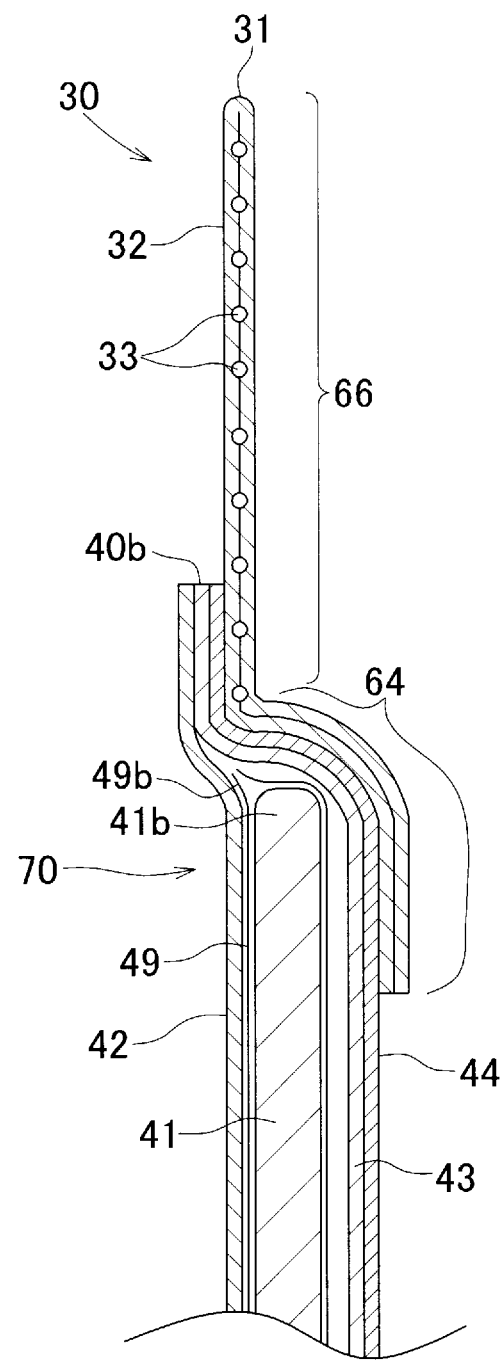
FIG. 8 is a partial diagram corresponding to FIG. 7 in a worn state.

Referring to FIG. 4, FIG. 7 and FIG. 8, outboard of the inelastic region 64 in the longitudinal direction Y, a second elastic region 66 is formed so as to exert the elasticity of the rear waist elastics 33, The second elastic region 66 is defined by the rear waist elastics 33 continuous between the lateral edges 30c of the rear waist panel 30. A dimension between one of a plurality of rear waist elastics 33 located closest to the crotch region 4 side in the second elastic region 66 and the rear end edge 41b of the core 41 in the longitudinal direction Y is to be about 5 to about 20 mm, preferably about 7 to about 15 mm.

Since the distance between the rear end edge 41b of the core 41 and the rear waist elastics 33 located outboard thereof in the longitudinal direction Y is defined as above, as illustrated in FIG. 8, when the rear waist panel 30 contracts in the lateral direction X, the second elastic region 66 comes into close contact with the wearer, while the core 41 floats up from the rear waist panel 30. At the rear end edge 41b of the core 41, a stiffness difference is made in space from the rear waist panel 30, hence a step part is formed in the rear waist panel 30 to which the rear end edge 41b is joined. In particular, since the gasket elastics 51 extending the longitudinal direction Y are overlapped at least with part of the rear waist elastics 33, the crotch panel 40 is contracted in the longitudinal direction Y, and thereby a step may more easily be generated in the rear waist panel 30.

The core 41 bends to a direction to be spaced away from the wearer's skin in the lateral direction X, and a step is formed by the rear waist panel 30 at the rear end edge 41b. Thus the core 41 and rear waist panel 30 form a pocket 70 to retain excretions such as feces or the like. The excretions are temporarily retained in the pocket 70, and thereafter fluid may be absorbed by the core 41. Thus in particular, it is possible to prevent soft stools with a high water content from leaking from the waist opening. By forming the pocket 70, the core 41 is spaced away from the wearer's skin so that it is possible to prevent the core 41 from staying in close contact with the wearer's skin via the body side liner 42 causing dampness or diaper rashes.

The second elastic regions 63, 66 of the front and rear waist panels 20, 30 are spaced apart from each other outboard of the covering sheet 49 in the longitudinal direction Y. More specifically, the front and rear waist elastics 23, 33 attached in the second elastic regions 63, 66 do not overlap with the front and rear end edges 49a, 49b of the covering sheet 49. The front and rear end edges 49a, 49b are located inner side than the front and rear waist elastics 23, 33 in the longitudinal direction Y. When a nonwoven fabric or the like in which fibers are mechanically entangled is used as the covering sheet 49, it may be a sheet having a relatively large bending stiffness and the sheet may be difficult to contract even by the contractile force of the elastics. However, since the front and rear waist elastics 23, 33 are not overlapped with the covering sheet 49, it is possible to ensure that the front and rear waist panels 20, 30 contract and to keep them in close contact with the wearer's body. Furthermore, in the rear waist panel 30, the second elastic region 66 is ensured to contract, hence the pocket 70 may be easily formed.

The front and rear waist panels 20, 30 include a two-folded sheet which is formed by folding back a piece of sheet. At the front and rear end edges 40a, 40b of the crotch panel 40, only the body side liner 42, the leakage-barrier sheet 43, and the back sheet 44 are overlapped. Therefore, in the region in which these front and rear waist panels 20, 30 and the front and rear end edges 40a, 40b of the crotch panel 40 are overlapped, a relatively small number of sheets, five in total, are overlapped. Since the number of overlapping sheets is small, the stiffness in this part is also relatively small, the front and rear waist panels 20, 30 are ensured to contract by the contractile force of the front and rear waist elastics 23, 33.

In this embodiment, the front and rear waist elastics 23, 33 are not located in the inelastic regions 61, 64. However, if the elasticity thereof is smaller than that of the first elastic regions 62, 65 so as not to contract the core 41, elastics may be attached.

It is possible to generate stiffness between the central portion thereof and lateral portions such that the core 41 bends easily in the lateral direction X. For example, the mass per unit area of the core 41 in the central portion in the lateral direction X may be differentiated from that on the lateral portions so that a difference in stiffness is obtained. The core 41 may include region(s) in which no or scarce core material is present. Furthermore, the core 41 may be subjected to a press work either in the central portion or on lateral portions so as to obtain a difference in stiffness. Also, a slit extending in the longitudinal direction Y or lateral direction X may be formed in the core 41 so as to partially lower the stiffness thereof.

The crotch panel 40 is attached with the distal elastics 52, which causes the second cuff 48 to contract in the longitudinal direction Y. Together with this, the entirety of the crotch panel 40 is contracted in the longitudinal direction Y. The vicinity of the rear end edge 41b of the core 41 is also contracted in the longitudinal direction Y, thereby forming the pocket 70 more easily. In this embodiment, the pocket 70 is formed in the rear waist region 3, however, it may be formed in the front waist region 2 or front and rear waist regions 2, 3.

The present invention described above may be arranged in at least one or more of the following features:

(i) A disposable wearing article having a longitudinal direction and lateral direction, including:
 a skin facing side and a non-skin facing side opposite thereto;
 front and rear waist regions;
 a crotch region extending between the front and rear waist regions;
 a first waist panel which defines one of the front and rear waist regions and is elastically contractible in the lateral direction;
 a second waist panel which defines the other of the front and rear waist regions and is elastically contractible in the lateral direction;
 a crotch panel extending between the first and second waist panels in the longitudinal direction to define a crotch region; and
 a body fluid absorbent structure located in the crotch panel, wherein:
 the body fluid absorbent structure includes a liquid-absorbent core and a liquid-permeable covering sheet covering the core;
 the crotch panel is provided with first and second panel-end edges extending in the lateral direction and joined on the skin facing side of the first and second waist panels respectively, and
 the core is provided with first and second core-end edges each extending in the lateral direction and at least the second end edge thereof overlaps with the second waist panel;
 the second waist panel is provided with an inelastic region defined in a region to be overlapped with the core, wherein a first elastic region is formed outboard of the inelastic region in the lateral direction and a second elastic region is formed outboard of the inelastic region in the longitudinal direction; and
 a distance between the second elastic region and the second core-end edge is 5 to 20 mm.

The aspect(s) of the present invention described in the above item (i) may include at least the following embodiments, which may be taken in isolation or in combination with one another:

(ii) The first and second elastic regions are defined by contractibly attaching a plurality of waist elastics extending in the lateral direction and spaced apart from one another in the longitudinal direction in a stretched state.
(iii) The crotch panel includes a pair of gasket cuffs extending in the longitudinal direction and located outboard of the lateral edges of the core in the lateral direction, wherein
 each gasket cuff is provided with gasket elastics extending in the longitudinal direction and contractibly attached in a stretched state, and
 at least a second end portion of first and second end portions of the gasket elastics overlaps with the first elastic region.
(iv) The second end portion of the gasket elastics is located inner than the second core-end edge in the longitudinal direction, and a distance between the second end portion of the gasket elastics and the second core-end edge in the longitudinal direction is 5 to 20 mm.
(v) A difference in stiffness in the core is formed in the lateral direction in a region overlapping with the second waist panel.
(vi) The first elastic region is partially overlapped with lateral edges of the core, respectively, and a dimension of a region overlapped in the lateral direction is 15 to 35 mm.
(vii) The second elastic region is spaced outward from the covering sheet in the longitudinal direction.

The described aspects and/or embodiments provide one or more of the following effects.

In the second waist panel, an inelastic region is formed in a region overlapping with the core; a first elastic region is formed on lateral portions thereof; a second elastic region is formed outboard thereof in the longitudinal direction; and a distance between the second elastic region and the second core-end edge is 5 to 20 mm. With such an arrangement, in a region in which the core is not overlapped, the second waist panel is in close contact with the wearer's body, while in a region in which the core is overlapped, the second waist panel may be spaced away from the wearer's body and a pocket may be formed in the vicinity of the second core-end edge. Since the excretions are retained in the pocket, it is possible to prevent such excretions from leaking out of the wearing article.

As each component of the diaper 1, a variety of known materials normally used in the relevant fields may be used without limit in addition to the material described in the description. The diaper 1 may be formed in such a manner that the front waist region 2, rear waist region 3 and crotch region 4 are continuously formed.

In the description and claims of the present invention, the terms "first" and "second" are used to merely distinguish the components, locations or the like having similar names. Furthermore, the terms "first waist region" means one of the front and rear waist regions, and "second waist region" means the other.

This application claims the benefit of Japanese Application No. 2011-218056 the entire disclosure of which is incorporated by reference herein.

The invention claimed is:

1. A disposable wearing article having in a developed plane view a longitudinal direction and lateral direction, comprising:
 a skin facing side and a non-skin facing side opposite thereto;
 front and rear waist regions;
 a crotch region extending between the front and rear waist regions;
 a front waist panel which defines the front waist region and is elastically contractible in the lateral direction;
 a rear waist panel which defines the rear waist region and is elastically contractible in the lateral direction;
 a crotch panel extending between the front and rear waist panels in the longitudinal direction to define a crotch region; and
 a body fluid absorbent structure located in the crotch panel, wherein:
 the body fluid absorbent structure includes a liquid-absorbent core and a liquid-permeable covering sheet covering the core;
 the crotch panel is provided with first and second panel-end edges extending in the lateral direction and joined on the skin facing side of the first and second waist panels respectively, and the core is provided with first and second core-end edges each extending in the lateral direction and at least the second core-end edge thereof overlaps with the rear waist panel;

the rear waist panel is provided with an inelastic region defined in a region overlapped with the core, wherein a first elastic region is formed outboard of the inelastic region in the lateral direction and a second elastic region is formed outboard of the inelastic region in the longitudinal direction; and a distance between the second elastic region and the second core-end edge is 5 to 20 mm, wherein the front waist panel includes a front waist sheet that is folded in half about a folding line that extends in the lateral direction toward the back side of the diaper and overlaps itself along the entire length thereof with front waist elastic elements attached between the folded portion of the front waist sheet, the rear waist panel includes a rear waist sheet that is folded in half about a folding line that extends in the lateral direction toward the back side of the diaper and overlaps itself along the entire length thereof with rear waist elastic elements attached between the folded portion of the rear waist sheet, the rear waist elastic elements do not extend into the inelastic region, and the crotch panel comprises a pair of gasket cuffs that extend in the longitudinal direction and are located outboard of the lateral edges of the core in the lateral direction, with each of the gasket cuffs being provided with gasket elastics that extend in the longitudinal direction and are contractibly attached in a stretched state, front and rear end portions of the gasket elastics overlap the front and rear waist regions respectively and intersect with the front and rear waist elastic elements.

2. The disposable wearing article according to claim 1, wherein the first and second elastic regions are defined by contractibly attaching a plurality of waist elastics extending in the lateral direction and spaced apart from one another in the longitudinal direction in a stretched state.

3. The disposable wearing article according to claim 2, wherein the crotch panel comprises a pair of gasket cuffs extending in the longitudinal direction and located outboard of the lateral edges of the core in the lateral direction, wherein each gasket cuff is provided with gasket elastics extending in the longitudinal direction and contractibly attached in a stretched state, and at least a second end portion of first and second end portions of the gasket elastics overlaps with the first elastic region.

4. The disposable wearing article according to claim 3, wherein the second end portion of the gasket elastics is located inner than the second core-end edge in the longitudinal direction, and a distance between the second end portion and the second core-end edge in the longitudinal direction is 5 to 20 mm.

5. The disposable wearing article according to claim 4, wherein a difference in stiffness in the core is formed in a region overlapping with the rear waist panel in the lateral direction.

6. The disposable wearing article according to claim 4, wherein the first elastic region is partially overlapped with lateral edges of the core, respectively, and a dimension of a region overlapped in the lateral direction is 15 to 35 mm.

7. The disposable wearing article according to claim 3, wherein a difference in stiffness in the core is formed in a region overlapping with the rear waist panel in the lateral direction.

8. The disposable wearing article according to claim 3, wherein the first elastic region is partially overlapped with lateral edges of the core, respectively, and a dimension of a region overlapped in the lateral direction is 15 to 35 mm.

9. The disposable wearing article according to claim 2, wherein a difference in stiffness in the core is formed in a region overlapping with the rear waist panel in the lateral direction.

10. The disposable wearing article according to claim 2, wherein the first elastic region is partially overlapped with lateral edges of the core, respectively, and a dimension of a region overlapped in the lateral direction is 15 to 35 mm.

11. The disposable wearing article according to claim 1, wherein the crotch panel comprises a pair of gasket cuffs extending in the longitudinal direction and located outboard of the lateral edges of the core in the lateral direction, wherein each gasket cuff is provided with gasket elastics extending in the longitudinal direction and contractibly attached in a stretched state, and at least a second end portion of first and second end portions of the gasket elastics overlaps with the first elastic region.

12. The disposable wearing article according to claim 11, wherein the second end portion of the gasket elastics is located inner than the second core-end edge in the longitudinal direction, and a distance between the second end portion and the second core-end edge in the longitudinal direction is 5 to 20 mm.

13. The disposable wearing article according to claim 12, wherein a difference in stiffness in the core is formed in a region overlapping with the rear waist panel in the lateral direction.

14. The disposable wearing article according to claim 12, wherein the first elastic region is partially overlapped with lateral edges of the core, respectively, and a dimension of a region overlapped in the lateral direction is 15 to 35 mm.

15. The disposable wearing article according to claim 11, wherein a difference in stiffness in the core is formed in a region overlapping with the rear waist panel in the lateral direction.

16. The disposable wearing article according to claim 11, wherein the first elastic region is partially overlapped with lateral edges of the core, respectively, and a dimension of a region overlapped in the lateral direction is 15 to 35 mm.

17. The disposable wearing article according to claim 1, wherein a difference in stiffness in the core is formed in a region overlapping with the rear waist panel in the lateral direction.

18. The disposable wearing article according to claim 17, wherein the first elastic region is partially overlapped with lateral edges of the core, respectively, and a dimension of a region overlapped in the lateral direction is 15 to 35 mm.

19. The disposable wearing article according to claim 1, wherein the first elastic region is partially overlapped with lateral edges of the core, respectively, and a dimension of a region overlapped in the lateral direction is 15 to 35 mm.

20. The disposable wearing article according to claim 1, wherein the second elastic region is spaced outward from the covering sheet in the longitudinal direction.

* * * * *